United States Patent [19]

Beckford et al.

[11] 4,030,980

[45] June 21, 1977

[54] APPARATUS AND METHOD FOR IDENTIFICATION OF SELECTED CLINICAL YEAST

[75] Inventors: Orville A. Beckford, Port Washington; Helen F. B. Dauzickas, Babylon Village, both of N.Y.

[73] Assignee: Corning Glass Works, Corning, N.Y.

[22] Filed: May 15, 1975

[21] Appl. No.: 577,799

[52] U.S. Cl. ............................................... 195/139
[51] Int. Cl.$^2$ ......................................... C12K 1/10
[58] Field of Search .................................. 195/139

[56] References Cited

UNITED STATES PATENTS

| | | | |
|---|---|---|---|
| 3,165,450 | 1/1965 | Scheidt | 195/139 |
| 3,179,574 | 4/1965 | Harrison | 195/139 |
| 3,597,326 | 8/1971 | Liner | 195/139 |
| 3,886,047 | 5/1975 | Billups | 195/139 |

*Primary Examiner*—Lionel M. Shapiro
*Assistant Examiner*—Robert J. Warden

[57] ABSTRACT

An apparatus for the identification of a number of the most frequently isolated medical yeasts employing a single tube and a multi-cavity plate. The tube contains sterile, liquid media to test for germ-tube production. The plate is composed of eleven, independently sealed peripheral wells, containing sterile solid media for the performance of urea, carbohydrate and nitrate tests. A central, optically transparent well contains corn-meal-tween agar for the morphological examination of the yeasts.

17 Claims, 9 Drawing Figures

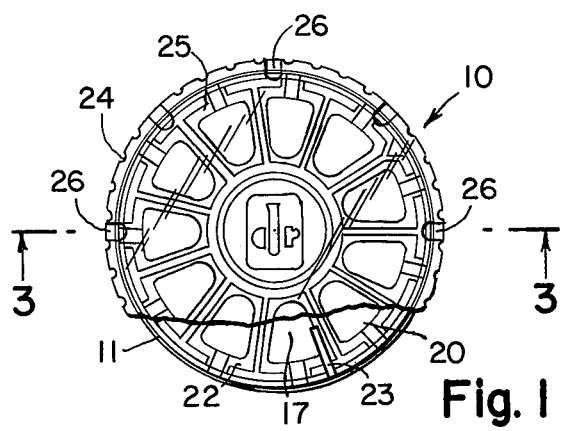
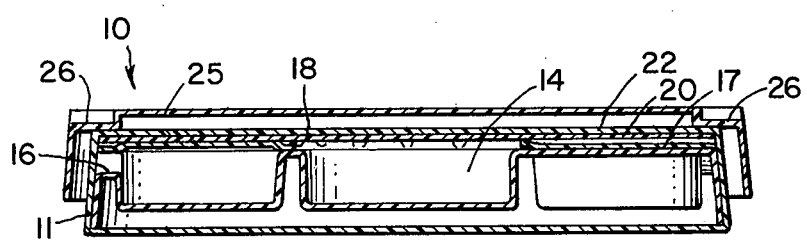
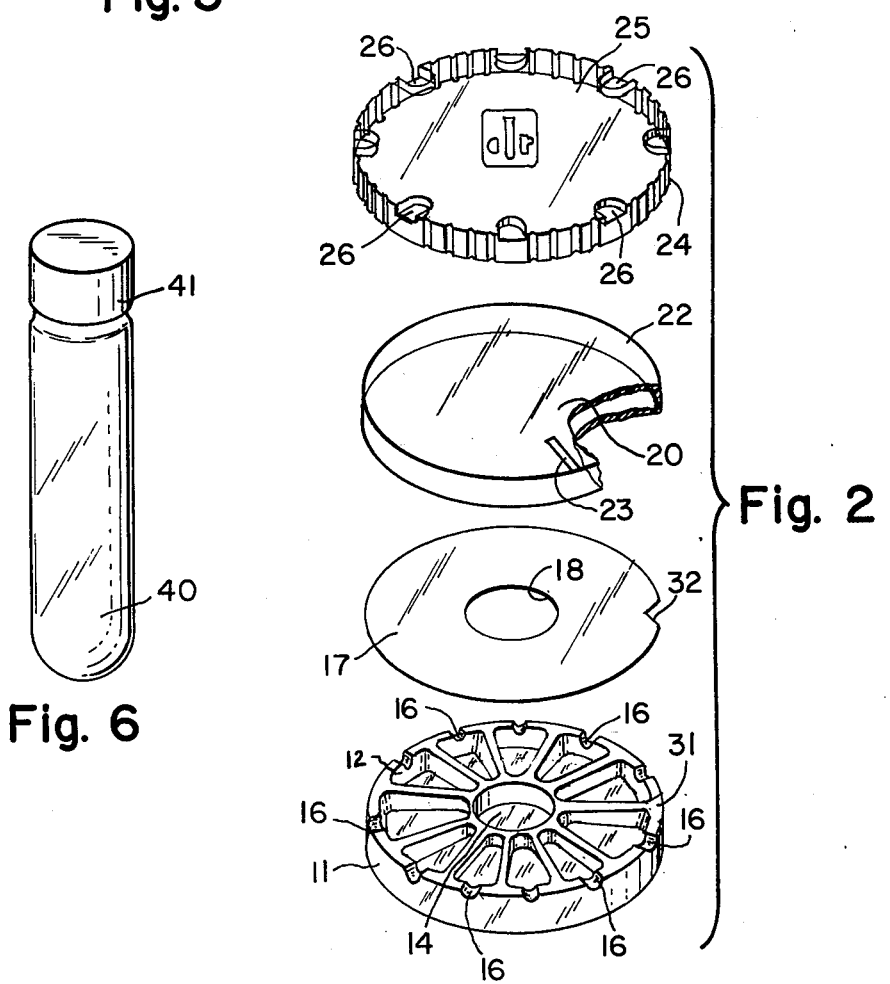

APPARATUS AND METHOD FOR IDENTIFICATION OF SELECTED CLINICAL YEAST

FIELD OF THE INVENTION

This invention relates to an apparatus and method for the identification of yeasts and other microorganisms.

BACKGROUND OF THE INVENTION

The present apparatus was devised to provide an apparatus useful for identification of organisms employing various media. One application of the apparatus is to identify medically important yeasts such as *C. albicans, C. stellatoidea, C. pseudotropicalis, C. tropicalis, C. guillermondii, C. parapsilosis, C. krusei, T. glabrata, S. cerevisiae, Tr. cutaneum Tr. pulluens, Cr. neoformans, Cr. laurentii, Cr. terreus, Cr. albidus, Geotrichum spp., R. glutinis* and *R. rubra*.

The scheme disclosed hereinafter to identify the aforementioned yeasts are based on data for reactions from "The Yeasts": 1971 J. Lodder (editor); "Identification of Yeasts": Webb, Papageorge and Hill, 1971; United States Public Health Service, Center for Disease Control Bullentin; and "A Guide to the Yeast and Yeast-Like Fungi of Medical Significance": Roth,F.

OBJECTS OF THE INVENTION

It is therefore an object of the present invention to provide an apparatus for the identification of a number of the most frequently isolated clinical yeasts.

It is another object of the present invention to provide an apparatus for identifying clinical bacteria utilizing a multicavity plate and single tube.

It is a further object of the present invention to provide a multi-cavity plate comprised of discrete wells readily adaptable to automatic loading of test media.

It is a still further object of the present invention to provide an improved multi-cavity plate including removable sterile seal means.

It is yet another object of the present invention to provide a multi-cavity media plate having discrete inoculation wells to permit visual and microscopic observation of culture growth that is readily mass produced by conventional vacuum molding, injection molding, blow molding and the like.

These and other objects, features and advantages of the present invention will, in part, be pointed out with particularity and will, in part, become obvious from the following more detailed description of the invention, taken in conjunction with the accompanying drawing, which forms an integral part thereof.

BRIEF DESCRIPTION OF THE DRAWING

In the various figures of the drawing like reference characters designate like parts.

In the drawing:

FIG. 1 is a plan view of the plate of this invention with the cover shown partially broken away;

FIg. 2 is a perspective view showing the components of the plate in an exploded relationship;

FIG. 3 is a section taken along line 3—3 of FIG. 1;

FIG. 6 is a perspective showing of the tube used in conjunction with the plate;

DESCRIPTION OF THE PREFERRED EMBODIMENT

Figure 4:
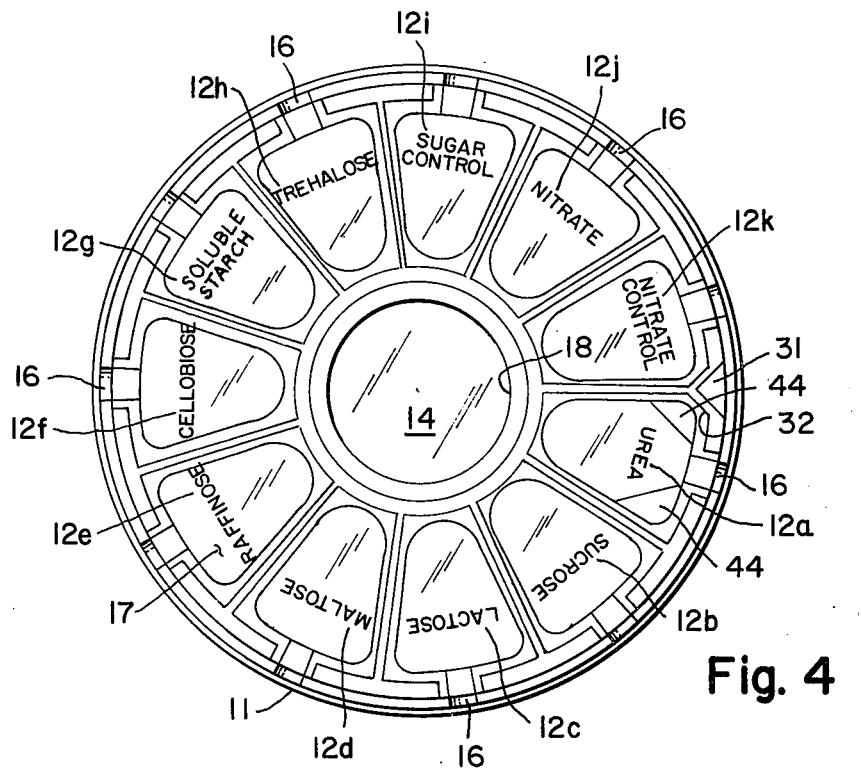
FIG. 4 is a top plan view of the plate with the cover removed.
Figure 5:
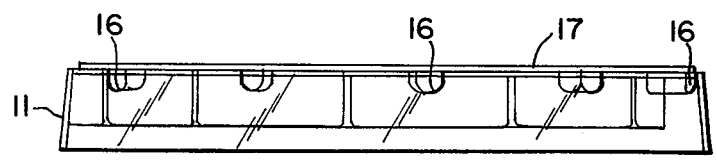
FIG. 5 is a side elevational view of the plate with the cover removed.

Referring now to the drawing, the apparatus shown generally by the numeral 10 is composed of a number of elements which may be vacuum formed out of thin plastic sheets. For example, 0.017 inch thick polyvinylchloride film has been found suitable for this purpose. For a better understanding of the invention the dimensions of the presently preferred embodiment is disclosed hereinafter. It is to be understood however that Applicants are not to be limited by the recitations of these dimensions. The diameter of the plate in one embodiment is 110 millimeters and is provided with 11 wells, each approximately 7 millimeters deep, 25 millimeters at one end and 10 millimeters at the other end. At the center there is a well 14 approximately 30 millimeters in diameter.

Each of the wells 12 is provided with an opening 16 for admittance of air. Sealed to the top of the plate 11, there is a thin transparent cover member 17. The cover member 17 is provided with a central opening 18 so as to expose well 14. Temporary protection of the well and sealing of the openings 16 is provided by a removable cover member 20. The member 20 may be a thin plastic shrink-fit tight-fitting envelope provided with an enclosed pull tape 23. When pull tape 23 is pulled the envelope comes off. After the cover is removed the individual wells 12 are sealed from the atmosphere except for the openings 16.

The removable cover member may be applied by heat sealing an envelope over it in a standard bag making machine and then passing the sealed envelope through a heat tunnel to shrink the film. Preferably, the envelope is round and formed by a round seal and cut off die so that a neat shrink pack results. The shrink pack film chosen should be permeable to ethylene oxide used for sterilization of the completed assembly.

Still other methods of protecting the central well 14 and closing the openings 16 may be employed as long as they are compatible with the maintaining of the sterility of the media contained therein.

Figures 7, 8, 9:
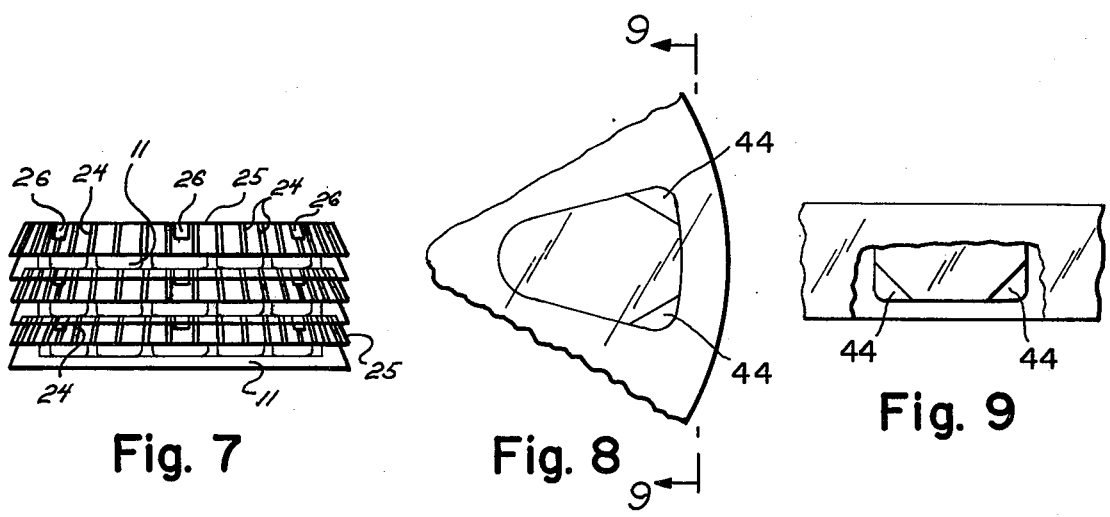
FIG. 7 is a plan view of a stack of plates.
FIG. 8 is a bottom plan view of a section of the apparatus.
FIG. 9 shows partially broken away a section taken along line 9—9 of FIG. 8.

The openings 16 are provided in the side of the wells so that gases emanating from the media which tend to rise are not readily diffused back into the openings of the other wells. It has been found that when the openings were placed on top of the wells significant diffusion between wells took place resulting in interference in reactions from well to well. Where the presence of oxygen was required, oxygen coming in between the outer wall and the cover rose to the chamber above the wells where it was trapped. On the other hand with the tubular side wall openings shown in the drawing the media was able to receive an adequate amount of oxygen. Opening size as well as position is important. They should be large enough for filling, inoculation, and oxygen, but small enough to prevent diffusion between adjacent chambers. A satisfactorily passage 16 has been found to be about 4.3 mm long and 6.4 mm wide and 2.6 mm high. A loose fitting cover or cap 25 is provided over the apparatus to provide protection during use, and tapered slightly toward the top to provide stability when stacked with other plates as shown in FIG. 7. Ribs 24 serve to stiffen cap 25 and permit air into openings 16 when bosses 26 serve as spacers to permit the free flow of air into openings 16 and well 14 when the device is in use. In an automatic loading device, the device not shown, loading of compartments or wells 12 is effected by needles inserted through apertures 16. The needles carry the several culture media for deposit thereof in respective wells. Indexing means, for example as shown in FIGS. 8 and 9 and discussed hereinafter can be used to lock plate 11 to the device for sequential or random loading of the wells. Such devices affording random or sequential orientation of plate 11 are common in the art with the drives thereof controlled by digital or analog signals. Cover member 17 is provided with a notch 32 that mates with boss 31 so that the device may be filled by an automatic filling machine, with the notch affording proper orientation of the cover member 17. The cover member 17 is labeled to show the contents of the particular wells. Respective wells are labeled illustratively as urea, sucrose, latose, maltose, raffinose, cellobiose, soluble starch, trehalose, sugar control, nitrate, and nitrate control. The tube 40, with a screw cap 41, shown in FIG. 6 is used to test for the induction of germ tubes, for example, by using isolated cultures of C. albicans and C. stellatoidea in an enriched environment.

When the plate 10 is inoculated with a suspension of a sterile pure culture and incubated at 25° for 2 to 10 days, yeasts present in the inoculum interact with the constituents of the media so that reactions may be ascertained visually in the eleven outer wells, and microscopically in the center well. The color differences in the outer wells are due to changes in indicator dyes (ph shifts) resulting from by-products of the yeasts reacting with another ingredient in the media. The media in the center well, when inoculated with a pure culture and covered with a sterile cover-slip, induces typical yeast morphology when examined microscopically.

| COMPONENTS OF THE APPARATUS | | Gms./100 ml solution |
|---|---|---|
| Tube 40 | | |
| | beef extract | 2.6 |
| | dextrose | 0.05 |
| Plate 10 | | |
| Well No. 12a — | UREA | |
| | agar | 1.5 |
| | bacto-area agar base | 2.9 |
| Well No. 12b — | SUCROSE | |
| | agar | 1.0 |
| | sucrose | 2.0 |
| | yeast nitrogen base | 0.67 |
| | pH indicator | 0.008 |
| Well No. 12c — | LACTOSE | |
| | agar | 1.0 |
| | lactose | 2.0 |
| | yeast nitrogen base | 0.67 |
| | pH indicator | 0.008 |
| Well No. 12d — | MALTOSE | |
| | agar | 1.0 |
| | maltose | 2.0 |
| | yeast nitrogen base | 0.67 |
| | pH indicator | 0.008 |
| Well No. 12e — | RAFFINOSE | |
| | agar | 1.0 |
| | raffinose | 4.0 |
| | yeast nitrogen base | 0.67 |
| | pH indicator | 0.008 |
| Well No. 12f — | CELLOBIOSE | |
| | agar | 1.0 |
| | cellobiose | 2.0 |
| | yeast nitrogen base | 0.67 |
| | pH indicator | 0.008 |
| Well No. 12g — | SOLUBLE STARCH | |
| | agar | 1.0 |
| | soluble starch | 1.0 |
| | yeast nitrogen base | 0.67 |
| | pH indicator | 0.008 |
| Well No. 12h — | TREHALOSE | |
| | agar | 1.0 |
| | trehalose | 2.0 |
| | yeast nitrogen base | 0.67 |
| | pH indicator | 0.008 |
| Well No. 12i — | SUGAR CONTROL | |
| | agar | 1.0 |
| | yeast nitrogen base | 0.67 |
| | pH indicator | 0.008 |
| Well No. 12j — | NITRATE | |
| | agar | 1.0 |
| | potassium nitrate | 2.0 |
| | yeast carbon base | 1.17 |
| | pH indicator | 0.008 |
| Well No. 12k — | CONTROL NITRATE | |
| | agar | 1.0 |
| | yeast carbon base | 1.17 |
| | pH indicator | 1.008 |
| Well No. 14 — | CENTER | |
| | corn meal agar | 1.7 |
| | tween 80 | 1.0 |

SUGGESTED TEST PROCEDURE

For each yeast isolated on standard sabouraud dextrose agar plates:

1. Bring plate 10 and tube 40 to room temperature.
2. Remove envelope seal 22 from edge of plate and discard.
3. Label a plate and a tube for identification.
4. Flame and air-cool a straight inoculating needle.
5. Pick up a small amount of an isolated yeast colony, taking care not to penetrate the agar surface.
6. Emulsify the yeast colony in a tube containing 5 cc sterile distilled water and mix well, using sterile technique.
7. Reflame the loop.
8. Check the suspension against a Wickerham card and adjust so that it reads just below 1+ (1+ means the lines can be distinguished, but has rough edges. Alternatively, read the suspension on a spectrophotometer at a wavelength of 540 nm using plain water as a blank. The suspension should give 70 ± 5% transmission.
9. Put a bulb onto the end of a sterile pasteur pipet.
10. Using the Pasteur Pipet asceptically withdraw approximately 1.5cc of the previous made suspension.
11. Via the channel 16 at the edge of each well, asceptically pipet one drop of the suspension into each of the eleven peripheral wells and replace the lid.
12. Using a sterile cooled mycological inoculating needle pick up another small amount of an isolated yeast colony, taking care not to penetrate agar surface.
13. Remove the lid from the plate 10.
14. Make one scratch into the surface of the agar in the center well of the plate with the end of the needle.
15. Streak across the scratch using the bend in the loop.
16. Reflame the loop.
17. Pick up a sterile round cover-slip with forceps and place it over the scratch on the center well.
18. Place the plate upright in a 25° C incubator and examine at 24 hours and then daily thereafter.
19. Discard cap 41 from tube 40.
20. Take pipet and touch colony
21. Place pipet into tube 40 and mix.
22. Place tube 40 in incubator for 2 hours incubation at 37° C.

READING OF REACTIONS

A. Tube

Transfer one drop of glucose-beef extract medium plus yeast to a microscope slide and a place a cover-slip on top. Observe the slide with a 10X objective for the production of germ tubes.

READING OF RESULTS

Plate

| | |
|---|---|
| Urea | positive: pink |
| | negative: straw colored |
| Sucrose | positive: yellow |
| | negative: purple |
| Lactose | positive: yellow |
| | negative: purple |
| Maltose | positive: yellow |
| | negative: purple |
| Raffinose | positive: yellow |
| | negative: purple |
| Cellobiose | positive: yellow |
| | negative: purple |
| Soluble Starch | positive: yellow |
| | negative: purple |
| Sugar Control | always purple |
| Nitrate Test | positive: blue or green |
| | negative: yellow |
| Nitrate Control | always yellow |
| Corn Meal | read microscopically |

INTERPRETATION OF REACTIONS

Follow key logic steps 1–15, defined below.

Key Logic

| TEST | | RESULTS | IDENTIFICATION | PROCEED TO TEST |
|---|---|---|---|---|
| 1. | Urease | Positive | | 10 |
| | | Negative | | 2 |
| 2. | Germ Tube | Positive | | 3 |
| | | Negative | | 4 |
| 3. | Sucrose | Positive | C. albicans | |
| | | Negative | C. stellatoidea | |
| 4. | Lactose | Positive | C. pseudotropicalis | |
| | | Negative | | 5 |
| 5. | Maltose | Positive | | 7 |
| | | Negative | | 6 |
| 6. | Trahalose | Positive | Tor. glabrata | |
| | | Negative | C. krusei or Geotrichum spp. | |
| 7. | Raffinose | Positive | | 8 |
| | | Negative | | 9 |
| 8. | Cellobiose | Positive | C. guillermondii | |
| | | Negative | S. cerevisiae | |
| 9. | Soluble Starch | Positive | C. tropicalis | |
| | | Negative | C. parapsilosis | |
| 10. | Corn Meal Tween | | Hyphae, pseudohyphae blastospores, and arthrospores | 11 |
| | | Non-pigmented colony Blastospores only | Cryptococcus spp. | 12 |
| | | Pigmented colony Blastospores only | Rhodotorula spp. | 15 |
| | | Pseudohyphae & Blastospores | C. krusei | |
| | | Pseudohyphae & Arthrospores | Geotrichum spp. | |
| 11. | Nitrate | Positive | Tr. pullulens | |
| | | Negative | Tr. cutaneum | |
| 12. | Nitrate | Positive | | 13 |
| | | Negative | | 14 |
| 13. | Sucrose | Positive | Cr. albidus | |
| | | Negative | Cr. terreus | |
| 14. | Lactose | Positive | Cr. laurentii | |
| | | Negative | Cr. neoformans | |
| 15. | Nitrate | Positive | Rh. glutinis | |
| | | Negative | Rh. rubra | |

There has been disclosed heretofore the best embodiments of the invention presently contemplated. However, it is to be understood that various changes and modifications may be made thereto without departing from the spirit of the invention.

What we claim as new and desire to secure by Letters Patent are:

1. Apparatus to grow and identify a number of isolated cultures including:
a plate including a plurality of discrete spaced wells defined by substantially vertical walls and an integral bottom wall,
a cover member disposed on said plate sealing the individual tops of said wells; and,
aperture means extending through a said vertical wall in communication with a respective one of each of said wells to expose the same to atmospheric air whereby a number of isolated cultures may be concomitantly grown.

2. The apparatus of claim 1, said plate including a central well around which said plurality of wells are radially spaced.

3. The apparatus of claim 2, a cap adapted to detachably sit upon and cover said plate, said cap including means spacing the same from said plate to permit air to pass therebetween and into said wells, through the aperture means, and central well.

4. The apparatus of claim 3, said spacing means comprising bosses formed in said cap to space the same from said plate when in detachable covering engagement therewith.

5. The apparatus of claim 3, including culture media disposed in each of said plurality of wells with said plate being substantially of circular cross section.

6. The apparatus of claim 1 including a seal means adapted to detachably sit upon said plate and air tightly cover said aperture means and thereby preserve the sterility and independent integrity of each of said plurality of spaced wells.

7. The apparatus of claim 6, wherein said seal means is a heat shrink film surrounding said plate.

8. The apparatus of claim 6, wherein the rim region of protective cover is adapted to fit under and be detachably held by said rim seal to afford added protection to said cover member and wells including said central one thereof.

9. The apparatus of claim 6, wherein said seal includes a tear strip to facilitate removal thereof from said plate.

10. The apparatus of claim 1, a protective cover detachably deposed over said central well to maintain the clinical integrity thereof.

11. The apparatus of claim 10, said protective cover substantially coextensive with the area of said plate to cover said wells radially spaced around said central one thereof.

12. The apparatus of claim 1 including means for indexing said plate to provide for the automatic loading of each of said plurality of wells through a respective one of said aperture means.

13. The apparatus of claim 12 wherein said indexing means includes one said well having an outer shape differing from that of the other said wells.

14. The apparatus of claim 1, wherein said cover member includes indicia carried thereon in registration with a respective one of said plurality of wells to indicate the contents thereof.

15. The apparatus of claim 1, wherein said plate and cover are formed of a transparent plastic.

16. The apparatus of claim 1, wherein the respective culture media deposited in each of said plurality of wells includes urea, sucrose, lactose, maltose, raffinose, cellobiose, soluble starch, trehalose, sugar control, nitrate and nitrate control media.

17. The apparatus of claim 16, in combination with a tube containing a sterile liquid media to test for the induction of germ tubes.

* * * * *